(12) United States Patent
Courtin et al.

(10) Patent No.: US 7,160,983 B2
(45) Date of Patent: *Jan. 9, 2007

(54) ECHINOCANDIN DERIVATIVES, THEIR METHOD OF PREPARATION AND THEIR APPLICATION AS ANTI-FUNGAL AGENTS

(75) Inventors: Olivier Courtin, Paris (FR); Patrick Fauveau, Livry Gargan (FR); Astrid Markus, Liederbach (DE); Dominique Melon Manguer, Montreuil (FR); Jean-Marc Michel, Compiegne (FR); Laurent Schio, Bondy (FR)

(73) Assignee: Aventis Pharma S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/666,072

(22) Filed: Sep. 19, 2003

(65) Prior Publication Data

US 2004/0072737 A1   Apr. 15, 2004

Related U.S. Application Data

(62) Division of application No. 09/581,451, filed as application No. PCT/FR98/02671 on Dec. 9, 1998, now Pat. No. 6,677,429.

(30) Foreign Application Priority Data

Dec. 10, 1997  (FR)  .................... 97 15628
Oct. 26, 1998  (FR)  .................... 98 13361

(51) Int. Cl.
    *C07K 7/50*  (2006.01)
(52) U.S. Cl. .................... 530/317; 514/11; 514/17; 530/329
(58) Field of Classification Search ............... 530/317, 530/329; 514/11, 17
    See application file for complete search history.

(56) References Cited

FOREIGN PATENT DOCUMENTS

| EP | 0 561 639 A1 | 9/1993 |
|---|---|---|
| EP | 0 736 541 | 10/1996 |
| GB | 2 241 955 A | 9/1991 |

*Primary Examiner*—David Lukton
(74) *Attorney, Agent, or Firm*—Charles A. Muserlian

(57) ABSTRACT

Compound of the formula

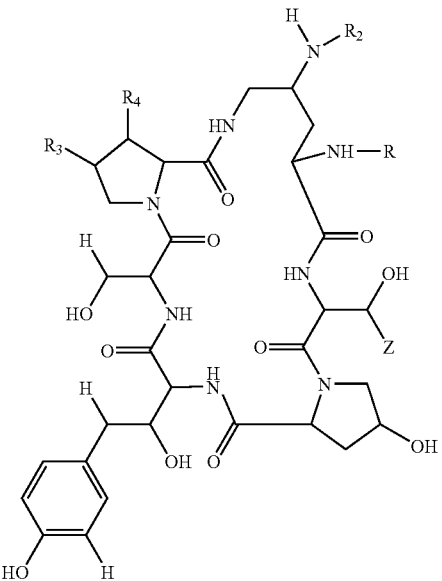

wherein $R_2$ is —$CH_2$—$CH_2$—$NH_2$, $R_3$ is —$CH_3$, $R_4$ is —OH, R is

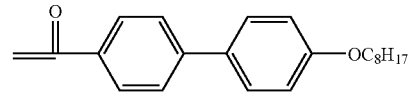

Z is methyl and salts thereof which are useful as antifungal agents.

11 Claims, No Drawings

ECHINOCANDIN DERIVATIVES, THEIR METHOD OF PREPARATION AND THEIR APPLICATION AS ANTI-FUNGAL AGENTS

This application is a division of U.S. patent application Ser. No. 09/581,451 filed Jun. 9, 2000, now U.S. Pat. No. 6,677,429, which is a 371 of PCT/FR98/02671 filed Dec. 9, 1998.

The present invention concerns novel echinocandin derivatives their method of preparation and their application as antifungal agents.

The invention has as its object, the compounds of formula (I), in any of the possible isomer forms as well as their compounds,:

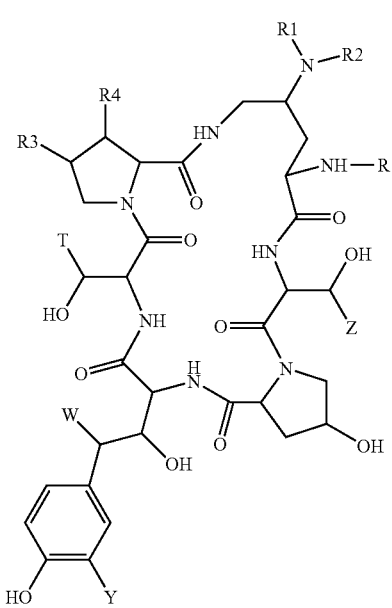

(I)

in which
either R1 and R2 identical or different from one another, represent a hydrogen atom, a hydroxyl radical, an alkyl radical containing up to 8 linear branched or cyclic carbon atoms, optionally interrupted by an oxygen atom optionally substituted by a
halogen atom, an OH radical, an

radical, a and b identical or different from one another, representing a hydrogen atom or an alkyl radical containing up to 8 carbon atoms, a and b optionally able with the nitrogen atom to form a heterocycle optionally containing one or several additional heteroatoms,
or else R1 forms a double bond with the endocyclic carbon atom carrying the radical

or else R2 represents
an $XR_a$ radical, X representing an oxygen atom or an NH or N-alkyl radical containing up to 8 carbon atoms and $R_a$ represents a hydrogen atom, a linear, branched or cyclic alkyl radical containing up to 8 atoms of carbon optionally substituted by one or several halogen atoms, by one or several OH, $CO_2H$ $CO_2$alc radicals,
by an

radical, a' and b' representing a hydrogen atom, an alkyl radical containing up to 8 carbon atoms, a' and b' able to form a heterocycle optionally containing one or several additional heteroatoms and/or by a heterocycle containing one or several heteroatoms or R2 represents a radical

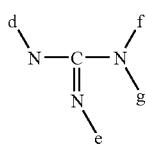

in which d, e, f, and g represent a hydrogen atom or an alkyl radical containing up to 8 carbon atoms, f and g able moreover to represent an acyl radical containing up to 8 carbon atoms, e and f able equally to form a ring optionally containing one or several heteroatoms,
R3 represents a hydrogen atom, a methyl or hydroxyl radical
R4 represents a hydrogen atom or a hydroxyl radical R representing a linear or branched or cyclic chain containing up to 30 carbon atoms, optionally containing one or several heteroatoms, one or several heterocycles or a linear, branched or cyclic acyl radical containing up to 30 carbon atoms optionally containing one or several heteroatoms and/or one or several heterocycles,
T represents a hydrogen atom, a methyl radical, a $CH_2CONH_2$, $CH_2C\equiv N$ radical, a $(CH_2)NH_2$ or $(CH_2)_2Nalc^+X^-$radical, X being a halogen atom and alc an alkyl radical containing up to 8 carbon atoms,
Y represents a hydrogen atom, a hydroxyl radical or a halogen atom or an OSO3H radical or one of the salts of this radical,
W represents a hydrogen atom or an OH radical,
Z represents a hydrogen atom or a methyl radical, as well as the addition salts with the acids of the products of formula (I).

Amongst the addition salts with the acids, those formed with mineral acids, such as hydrochloric, hydrobromic, sulphuric or phosphoric acids or the organic acids like formic, acetic, trifluoroacetic, propionic, benzoic, maleic, fumaric, succinic, tartaric, citric, oxalic, glyoxylic, aspartic, alkanesulphonic, such as sulphonic methane or ethane, arylsulphonic acids like the benzene or paratoluenesulphonic acids can be cited.

In the definition of the substituents,
the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl, or cyclohexyl radical,
the halogen is preferably fluorine or chlorine or bromine,
the aryl radical is preferably the radical phenyl,
the heterocyclic radical is preferably the pyrrolyle, pyrrolidinyl, pyridyl, pyrazinyl, pyrimidyl, piperidinyl, piperazinyl, quinuclidinyl, oxazoyl, isoxazoyl, morpholinyl, indolyl, imidozoyl, benzimidazoyl, triazoyle, thiazolyl, azetidinyl, aziridinyl radical.
as a salt of the SO3H radical, sodium, potassium salts or even the salts of amines can in particular be cited.

Amongst the preferred compounds of the invention:
the compounds of formula (I), in which T represents a hydrogen atom,
the compounds of formula (I), in which Y represents a hydrogen atom,
the compounds of formula (I), in which W represents a hydrogen atom,
the compounds of formula (I), in which Z represents a methyl radical,
the compounds of formula (I), in which R3 represents a methyl radical,
the compounds of formula (I), in which R4 represents a hydroxyl radical
the compounds of formula (I), in which R represents a radical can be especially cited.

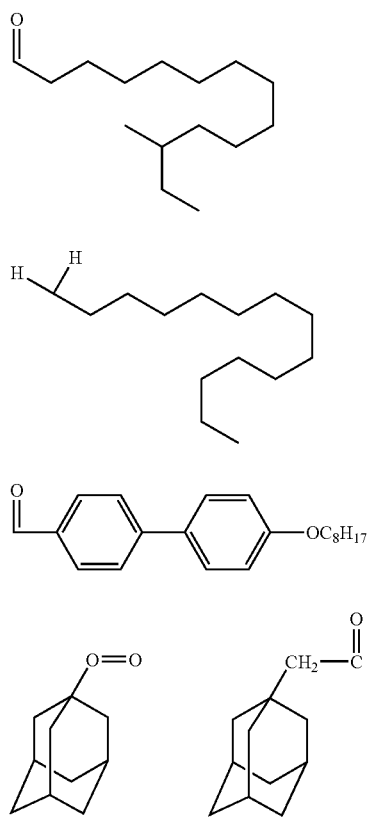

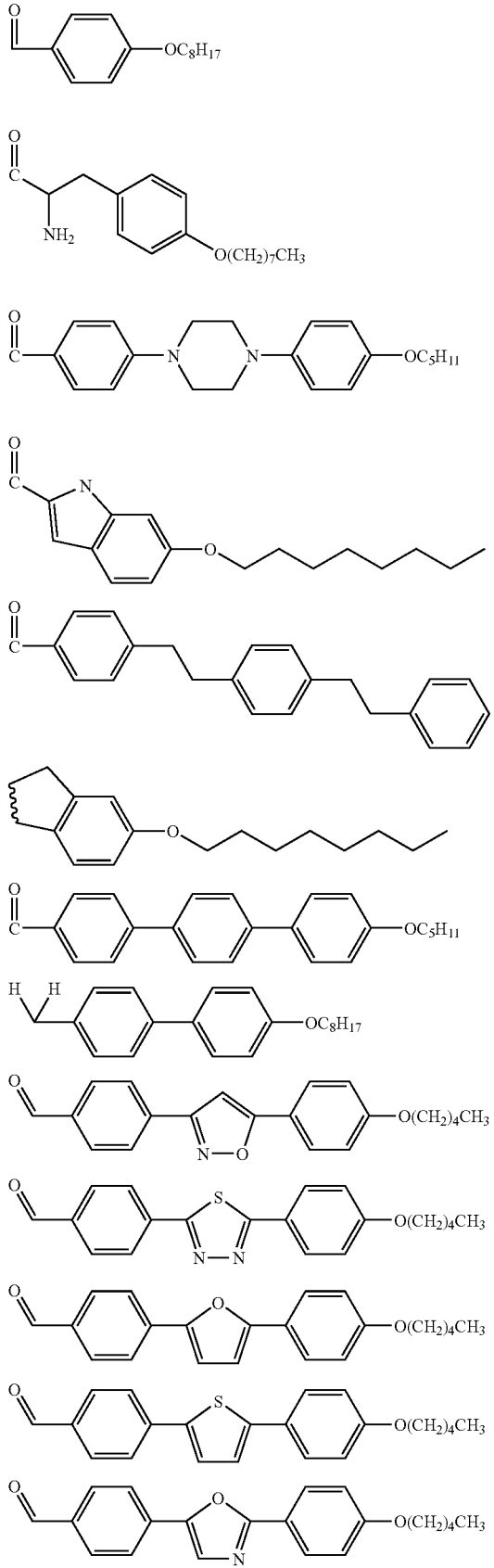

and more particularly those in which R represents a chain

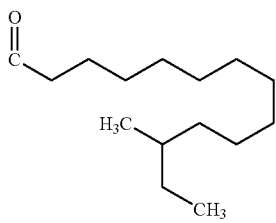

or those in which R represents a chain

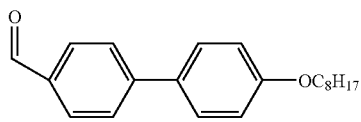

the compounds of formula (I) in which R1 forms with the endocyclic carbon atom carrying the NR1R2 radical, a double bond, and notably those in which R2 represents the radical

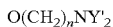

in which n represents an integer between 1 and 8 and very particularly those in which n represents the number 2 and Y' represents a hydrogen atom or an alkyl radical containing up to 8 carbon atoms, and those in which R represents a radical

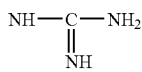

The invention has equally particularly as its object the compounds of formula (I) in which R2 represents a radical

in which Y" represents a hydrogen atom or an alkyl radical containing up to 8 carbon atoms and p represents an integer varying from 1 to 8 and especially the compounds in which p represents the number 2.

The invention has very particularly as its object, compounds in which R1 represents a hydrogen atom. Amongst the preferred compounds of the invention, the products of examples 8, 9, 11, 13 and 14 can be cited.

The compounds of formula (I) present significant anti-fungal properties; they are active notably on *Candida albicans* and other *Candida* like *Candida glabrata, krusei, tropicalis, pseudotropicalis, parapsilosis* and *Aspergillus fumigatus, Aspergillus flavus, Cryptococcus neoformans*.

The compounds of formula (I) can be used as medicines in man or animal, to fight against notably digestive urinary, vaginal or cutaneous candidoses, cryptococcoses, for example neuromenengeal, pulmonary or cutaneous cryptococcoses, bronchopulmonary and pulmonary aspergilloses and invasive aspergilloses of immunocompromise.

The compounds of the invention can be equally used in the prevention of mycosic ailments in people with congenital or acquired immune compromise.

The compounds of the invention are not limited to a pharmaceutical usage, they can be equally used as fungicides in domains other than pharmaceutical.

The invention thus has as its object as anti-fungal compounds, the compounds of formula (I) as well as their addition salts with the acids.

The invention equally has as its object the compounds of formula (I), as medicines.

The invention has very particularly as its object pharmaceutical compositions containing at least one compound of formula (I) or one of its addition salts with pharmaceutically acceptable acids as active ingredient.

These compounds can be administered by oral, rectal, parenteral route or by local route by topical application on the skin and the mucous membranes, but the preferred route is the oral route.

They can be solid or liquid and be presented in pharmaceutical forms currently used in human medicine, like for example, simple or sugar coated tablets, capsules, granules, suppositories, injectable preparations, ointments, creams, gels; they are prepared following usual methods. The active ingredient(s) can be incorporated into excipients usually used in these pharmaceutical compositions, like talc, gum arabic, lactose, starch, magnesium stearate, cocoa butter, aqueous or non aqueous mediums, fatty bodies of animal or vegetable origin, paraffin derivatives, glycol, various diluting, dissolving or emulsifying agents, preservatives.

These compositions can equally be presented in the form of a powder intended to be dissolved extemporarily in an appropriate medium, for example apyrogenic sterile water.

The administered dose varies according to the ailment treated, the subject concerned, the route of administration and the considered product. It can, for example, consist of between 50 and 300 mg per day by oral route, in adults for the products of examples 8, 9, 11, 13 and 14.

The invention equally has as its object a method of preparation of formula (I) compounds, characterised in that a formula (II) compound is submitted:

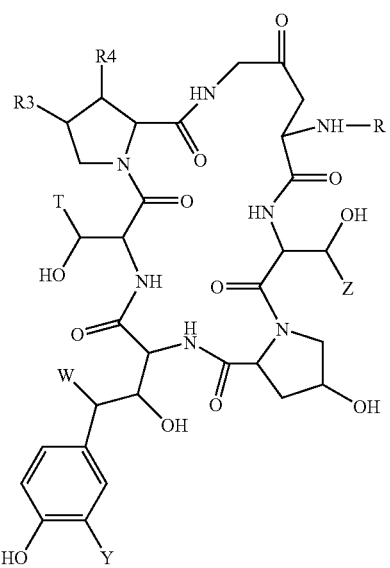

(II)

in which R, R3, R4, T, W, Y and Z retain their prior meaning, with the action of an amine or an amine derivative likely to introduce

the radical
in which R1 and R2 retain their prior meaning and if desired
the action of a reduction agent
and/or a functionalisation agent of the amine,
and/or an acid to form the salt of the obtained product,
and/or a separation agent of the different isomers obtained,
and thus obtains the sought formula (I) compound

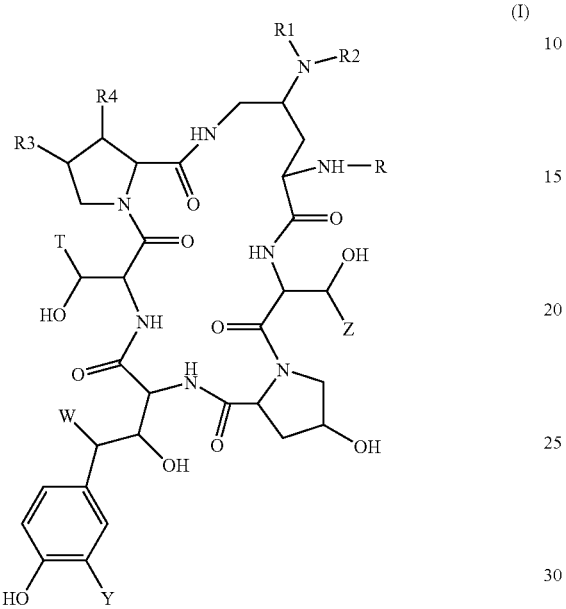

(I)

in which R1, R2, T, W, Y, R and Z retain their prior meaning in all of its possible isomer forms as well as their compounds and/or in the form of salts with the acids.

The formula (II) compounds used as initial compounds of the process of the invention are novel products and are themselves an object of the present invention, their preparation given in the experiment section can be schematised as follows:

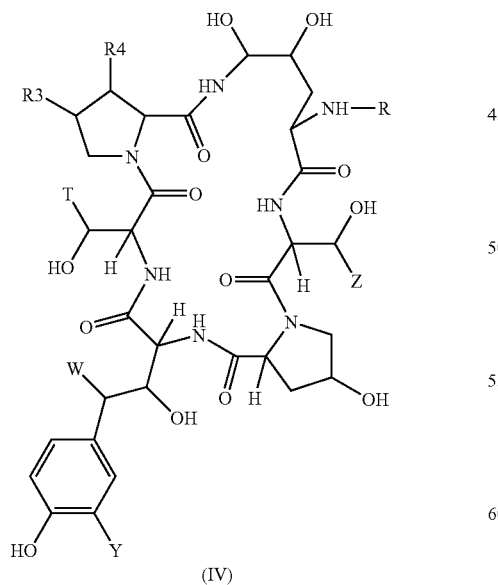

(IV)

| NaI/CH3CN/ClSi(CH3)3
| ou ISi(CH3)3/CH3CN

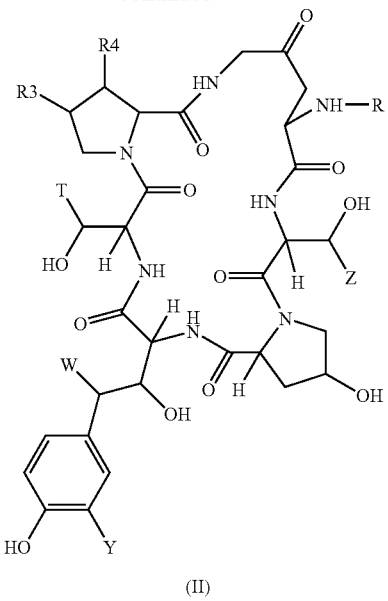

(II)

Isi-$(CH_3)_3$ or any other Lewis acid can be used.

A detailed example of the preparation of the compound of formula (II) is given in the experiment section, and the invention has more particularly as its object as novel chemical product 1-[4-oxo-N2-(12-methyl-1-oxotetradecyl) L-ornithine]4-[4-(4-hydroxyphenyl)-L-threonine}-5-L-serine-echinocandin B.

The product (IV) corresponding to the initial product of preparation 1 is a known product described and claimed in the European patent 438813.

The following examples illustrate the invention without at the same time limiting it.

The invention equally has as its object a preparation process characterised in that a formula (II) compound is submitted

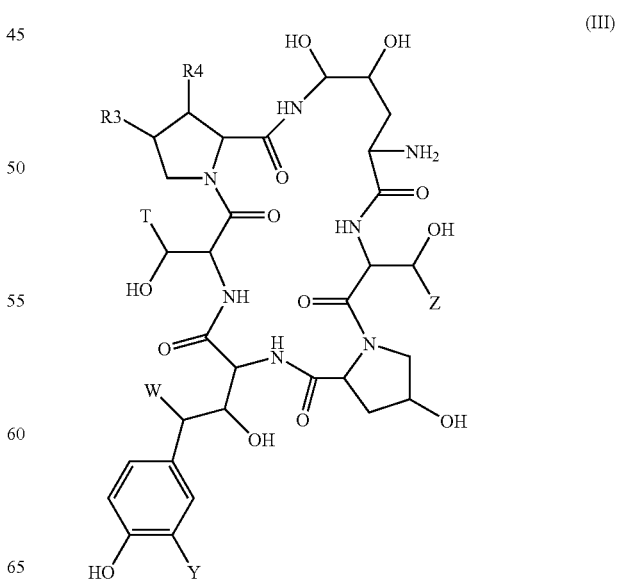

(III)

in which the different substituents retain their prior meaning with the action of an agent capable of replacing $NH_2$ with NHR, R retaining its prior meaning to obtain the formula (IV) compound

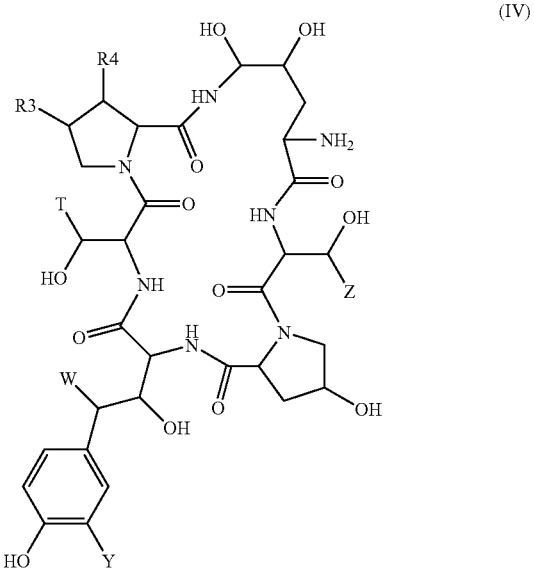

(IV)

in which the different substituents retain their prior meaning and are submitted to the action of silyl trimethyl iodide to obtain the compound of formula (II).

The compounds of formula (III) used as initial products are novel products and are themselves an object of the present invention. An example of preparation of the formula (III) compound is given hereafter in the experiment section.

The invention has more particularly as its object the deoxymulundocandin nucleus, compound of formula (III) the preparation of which is given hereafter in the experiment section.

The formula (IV) compounds as described above, with the exception of mulundocandin and deoxymulundocandin are novel products and are in themselves an object of the present invention.

The invention has more particularly as its object the compounds of formula (IV) whose preparation is given in the experiment section.

These following examples illustrate the invention without at the same time limiting it.

PREPARATION 1

1-[N2-(12-methyl-1-oxotetradecyl)-4-oxo-L-ornithine]4-[4-(4-hydroxyphenyl)-L-threonine]-5-L-serine echinocandin B 1 g of 1-[(4R,5R)-4,5-dihydroxy-N2-(12-methyl-1-oxotetradecyl)-L-ornithine]4-[4-(4-hydroxyphenyl)-L-threonine]-5-L-serine echinocandin B is introduced under magnetic stirring and under nitrogen atmosphere into 25 ml of acetonitrile. 455 µl of trimethylsilyl iodide is added. It is heated at 55° C. for 40 minutes. It is hydrolysed with a solution of sodium thiosulphate at 3%. After 10 minutes of stirring, it is dried under reduced pressure and purified by chromatography on silica. 62% of sought product is obtained.

CCM: rf=0.25 (eluent: $CH_2Cl_2$—MeOH—$H_2O$ 86-13-1).

EXAMPLE 1

Trifluoroacetate of 1-[4-amino-N2-(12-methyl-1-oxotetradecyl)-L-ornithine]4-[4-(4-hydroxyphenyl)-L-threonine]-5-L-serine echinocandin B (isomer B)

50 mg of the product of preparation 1 is introduced into 2.5 ml of methanol in the presence of 4A activated siliporite. 158 mg of ammonium acetate at 20° C. is added. The obtained solution is heated at 50° C. and 5.5 mg of $NaBH_3CN$ is added. It is stirred for 3 hours 15 minutes. 1 ml of distilled water is added and the solution is concentrated dry. 166 mg of product is obtained that is purified by HPLC ($C_{18}$) by eluting with the compound $CH_3CN$—$H_2O$—TFA (50-50-0.02). 17 mg of sought product is obtained.

$MH^+$=975.

EXAMPLE 2

Trifluoroacetate of 1-[4-[[2-dimethylaminoethyl-amino-N2-(12-methyl-1-oxotetradecyl)-L-ornithine] 4-[4-(4-hydroxyphenyl)-L-threonine]-5-L-serine echinocandin B (isomers A and B)

80 mg of the product of preparation 1, is introduced at 20° C. into a solution containing 1 ml of methanol, 160 µl of 2-dimethyl-aminoethylamine, 8 ml of a solution 1M of hydrochloric acid in methanol in the presence of 4A siliporite. 35 mg of sodium cyanoborohydrure is introduced and stirred for 20 hours at 20° C. It is filtered, washed in methanol and concentrated dry. 325 mg of product are obtained that is purified by HPLC ($C_{18}$) (eluent: $CH_3CN$—$H_2O$-TFA 45-55-0.02 then $CH_3CN$—$H_2O$-TFA 42-58-0.02). 8.1 gmg of sought isomer A product and 9.4 mg of isomer B sought product are obtained.

Mass Spectrometry: $MH^+$=1046 $MNa^+$=1068

EXAMPLE 3

Trifluoroacetate of 1-[4-[(3-aminopropyl)amino]-N2-(12-methyl-1-oxotetradecyl)-L-ornithine]4-[4-(4-hydroxy-phenyl)-L-threonine]-5-L-serine echinocandin B (A and B isomers)

30 cm3 of a 1M solution of hydrochloric acid is added at 0° C. in methanol into a solution containing 200 mg of the product of preparation 1, 2 ml of methanol and 300 µl of diaminopropane. It is stirred for 15 minutes at 0° C. and 84 mg of sodium cyanoborohydrure at 95% is added. It is stirred for 6 hours at ambient temperature and dried under reduced pressure. The obtained residue is made into a paste in acetonitrile, spun and dried under reduced pressure. 312 mg of product that is purified by HPLC ($C_{18}$) (eluent: $CH_3CN$—$H_2O$-TFA 45-55-0.02) and 15 mg of isomer A and 10 mg of isomer B is obtained.

Mass Spectrometry: $MH^+$=1032.

EXAMPLE 4

(Z+E) Trifluoroacetate of 1-[4-[(4.5-dihydro-1H-imidazol-2-yl)hydrazono]-N2-(12-methyl-1-oxotetradecyl)-L-ornithine]4[-4-(4-hydroxyphenyl)-L-threonine]-5-L-serine echinocandin B 350 mg of the product of preparation 1, 12 ml of methanol and 130 mg of 2-hydrazino 2-imidazoline hydrobromide is kept at reflux for 2 hours whilst stirring. After evaporating dry, 510 mg of product is obtained that is purified by chromatography on silica by eluting with a mixture $CH_2$—$Cl_2$—, MeOH—, $H_2O$ (86-13-1) then by semi-preparative ($C_{18}$) HPLC by eluting with a mixture of $CH_3CN$—, $H_2O$—, TFA (55-45-0.02). 133 mg of sought product is thus obtained.

Mass spectrometry: $MH^+=1056$ $MNa^+=1078$

EXAMPLE 5

(Z) 1-[4-[(2-Hydroxyethoxy)imino]-N2-(12-methyl-1-oxotetradecyl)-L-ornithine]4-[4-(4-hydroxyphenyl)-L-threonine]-5-L-serine echinocandin B and corresponding E isomer A mixture of 36 mg of O-(2-hydroxyethyl)hydroxylamine, 5 ml of ethanol, 12 μl of pyridine, 4 μl of pure acetic acid and 150 mg of the product of preparation 1 is kept at reflux for 4 hours. 205 mg of product that is purified by chromatography on silica by eluting with the methylene chloride-methanol-water (86-13-1) mixture. 2 products of rf=0.2 and 0.25 (isomer Z and isomer E) are isolated.

Mass spectrometry: $MH^+=1033$ $MNa^+=1055$

EXAMPLE 6

(E) 1-[4-(hydroxyimino)-N2-(12-methyl-1-oxotetradecyl)-L-ornithine]4-[4-(4-hydroxyphenyl)-L-threonine]-5-L-serine echinocandin B and corresponding Z isomer A mixture containing 200 mg of the product of preparation 1,8 ml of ethanol, 36 mg of hydroxylamine hydrochloride is left for 1 hour at reflux whilst stirring. It is dried and purified by chromatography HPLC ($C_{18}$) (eluent $CH_3CN$—$H_2O$ 60-40). 72 mg of Z isomer and 60 mg of E isomer is obtained.

Mass spectrometry: $MH^+=989$ $MNa^+=1011$

EXAMPLE 7

Trifluoroacetate of 1-[4-(hydroxyamino)-N2-(12-methyl-1-oxotetradecyl)-L-ornithine]4-[4-(4-hydroxyphenyl)-L-threonine]-5-L serine echinocandin B (isomer A and isomer B)

70 mg of E+Z oxime mixture obtained in the previous example, 1 cm³ of trifluoroacetic acid, 12 mg of sodium cyanoborohydrure at 95% mixture is stirred for 3 hours. It is dried under reduced pressure. It is purified by HPLC ($C_{18}$). The products sought are obtained.

Mass spectrometry: $MH^+=991$ $MNa^+=1013$

EXAMPLE 8

(Z) Chlorohydrate of 1-[(S)-N2-(12-methyl-1-oxotetradecyl)-4-[[(3-piperidinyl)oxy]imino]-L-ornithine]4-]4-(4-hydroxyphenyl)-L-threonine]-5-L serine echinocandin B Stage A:

146 mg of the product of preparation 1 and 60 μl of acetic acid is added to a solution containing 45 mg of R-3-(aminooxy)-1-piperidine phenylmethyl carboxylate and 2 ml of methanol. It is stirred for 2 hours at ambient temperature. It is concentrated, purified by chromatography on silica by eluting with the 98-2 methylene chloride-methanol compound. The sought product is thus obtained.

Mass spectrometry: $MH^+=1206$ $MNa^+=1228$

Stage B:

A compound containing 61 mg of the product prepared in stage A, 20 mg of palladium on carbon and 1 ml of acetic acid is placed under hydrogen atmosphere and stirred vigorously for 5 hours. It is filtered and concentrated. 65% of sought product is obtained.

Mass spectrometry: $MH^+=1072$

EXAMPLE 9

Trifluoroacetate of 1-[4-[(2-aminoethyl) amino]-N2-(12-methyl-1-oxotetradecyl)-L-ornithine]4-[4-(4-hydroxyphenyl)-L-threonine]-5-L serine echinocandin B (isomer A and isomer B)

To the solution of 300 mg of preparation 1 in 6 ml of methanol in the presence of 375 μl of ethylenediamine is added 63 ml of a solution of 1M of hydrochloric acid in methanol. After 15 minutes of agitation, 126 mg of sodium cyanoborohydrure ($NaBH_3CN$) is added. The reaction medium is stirred for 5 hours. It is filtered and dried, the products purified by HPLC ($C_{18}$) by eluting with the $CH_3CN$—$H_2o$-TFA (40-60-0.02) mixture. The sought products are thus obtained.

Mass spectrometry: $MH^+=1018$ $MNa^+=1040$

EXAMPLE 10

(E) 1-[4-[(2-bromoethoxy) imino)-N2-(12-methyl-1-oxotetradecyl)-L-ornithine]4-[4-(4-hydroxyphenyl)-L-threonine]-5-L-serine echinocandin B and corresponding Z isomer 402 mg of bromo-2-ethoxyamine bromhydrate is added to a solution containing 710 mg of the product of preparation 1 and 28 ml of absolute methanol. The mixture is brought to reflux for 55 minutes. It is concentrated under reduced pressure. The obtained product is purified by flash chromatography on silica by eluting with the (9-1) methylene chloridemethanol compound. The sought products isomer A: Rf=0.54, isomer B: Rf=0.47 are obtained.

Mass spectrometry: $MH^+=1095$ $MNa^+=1117$

EXAMPLE 11

(±) Trifluoroacetate of 1-[4-[(aminoiminomethyl) hydrazono]-N2-(12-methyl-1-oxotetradecyl)-L-ornithine]4-[4-(4-hydroxyphenyl)-L-threonine]-5-L serine echinocandin B 162 mg of aminoguanidine hydrochloride is added to a solution containing 260 mg of the product of preparation 1 and 10 ml of n-butanol. The reaction medium is brought to reflux for 2 hours 30 minutes. It is concentrated under reduced pressure. The obtained product is purified by semi-preparative HPLC. 225 mg of product in a 50/50 mixture of isomers is obtained.

Mass spectrometry: $MH^+=1030$ $MNa^+=1052$

EXAMPLE 12

(Z) Trifluoroacetate of 1-[4-[[2(dimethylamino) ethoxyimino]-N2-(12-methyl-1-oxotetradecyl)-L-ornithine]4-[4-(4-hydroxyphenyl)-L-threonine]-5-L-serine echinocandin B and corresponding E isomer 80.5 mg of the product of example 10 are introduced into 32 ml of an ethanolic solution of dimethylamine. The reaction medium is brought to reflux for 45 minutes. It is concentrated. The obtained product is purified by HPLC ($C_{18}$) ($CH_3CN$—$H_2O$-TFA 60-40-0.02). The sought products are thus obtained.

Mass spectrometry: $MH^+$=1060

EXAMPLE 13

(E) Trifluoroacetate of 1-[4-[[2-aminoethoxy)-imino]-N2-(12-methyl-1-oxotetradecyl)-L-ornithine]4-[4-(4-hydroxyphenyl)-L-threonine]-5-L-serine echinocandin B and corresponding Z isomer 50 mg of the product of example 10 is introduced into ammonia. It is stirred under pressure for 16 hours whilst allowing it to come to ambient temperature. The reaction medium is again placed in the (45-55) $CH_3CN$—$H_2O$ compound to be purified by HLPC ($C_{18}$). The sought products are obtained.

Mass spectrometry: $MH^+$=1032.

Preparation 2: deoxymulundocandin "nucleus"

2 g of deoxymulundocandin are dissolved in 20 ml of DMSO. This solution is poured into a suspension containing 120 g of FH2264 Utahensis actinoplanes in 870 ml of a $KH_2PO_4$, $K_2HPO_4$ (pH: 6.8) buffer. The reaction medium is stirred for 70 hours at 30° C. It is filtered. The mycelium is washed with the phosphate buffer (pH: 6.8). The washing liquids and the filtrate are joined. The obtained product is chromatographed on a DIAION HP 20, resin and a product is obtained that is used as hereafter.

EXAMPLE 14

Trifluoroacetate of 1-[4-[(2-aminoethyl) amino]N2-[[4'-(octyloxy)[1.1'-biphenyl]-4-[carbonyl]-L-ornithine]4-[4-(4-(4-hydroxyphenyl)-L-threonine]-5-L serine echinocandin B (isomer A)

Stage A: 1-[(4R,5R)-4.5-dihydroxy-N2-[[4'-(octyloxy)[1.1'-biphenyl]-4-yl]carbonyl]-L-ornithine]-4-[4-hydroxyphenyl)-L-threonine]-5-L-serine echinocandin B 1-Preparation of the Ester 632 g of 2.3.4.5.6 pentafluorophenol is added in 695 mg of N,N'-dicyclohexylcarbodiimide to 1 g of 4'-octyloxy-[1.1'-biphenyl]4-carboxylic acid in 22 ml of tetrahydrofurane, stirred for 22 hours at ambient temperature, filtered, the solvents are eliminated under reduced pressure, the residue is placed into ether, stirred at about 35° C., filtered, the solvent is evaporated, it is dried and 1.46 g of expected product is obtained, used as it is.

2-Coupling 677 mg of deoxymulundocandin <<nucleus>> obtained in preparation 2 is introduced, into 16 ml of DMF. The obtained solution is stirred for 5 minutes and 793 g of 4'-(octyloxy)-[1.1'-biphenyl-4-pentafluorophenyl carboxylate obtained above is added.

The reaction compound is stirred and kept under nitrogen atmosphere for 24 hours. It is filtered and concentrated. The residue is placed into ether, triturated, stirred for 25 minutes, spun, washed with ethylic ether, chromatographed on silica by eluting with the (86/13/1) then (80/20/1) methylene chloride, methanol, water mixture. The sought product is thus obtained. Yield 73%.

Stage B:1-[N2-[[4'-(octyloxy)-[1.1'-biphenyl]-4-yl]carbonyl-4-oxo-L-ornithine]-4-[4-(4-hydroxyphenyl)-L-threonine]-5-L-serine-echinocandin B 311 µl of trimethylsilyl iodide is added to a suspension containing 809 mg of the product of stage A and 19 ml of acetonitrile. The reaction medium is stirred for 15 minutes at 60° C. under nitrogen atmosphere. The compound is poured into a sodium thiosulphate saturated solution. The residue obtained is evaporated and chromatographed on silica, by eluting with the 86/13/1 methylene-chloride methanol water compound. The sought product is obtained. Yield 55%.

Stage C: 1-[4-[(2-aminoethyl) amino]-N2-[[4'-(octyloxy)[1.1'-biphenyl]-4-yl]carbonyl]-L-ornithine]-4-[4(4-hydroxyphenyl)-L-threonine]-5-L serine echinocandin B (isomer A) trifluoroacetate 560 µl of acetic acid are added to a solution containing 900 mg of the product of the preceding stage, 16 ml of methanol and 250 µl of diamine ethylene. It is stirred for 15 minutes and 64 mg of sodium cyanoborohydrure is added. It is stirred for 18 hours. It is filtered and concentrated. The residue is placed in a minimum of water, triturated, spun and purified by preparative HPLC by eluting with the compound $CH_3CN$/$H_2O$/TFA/(55-45-0.2). The sought product is obtained. Yield 26%.

Spectrum RMN $CDCl_3$ 9.07 (m wide) 1H; 8.48 (dl, J=8) 1H; 8.00 (dl, J=8) 2H; 7.96 (dl, J=8.5) 2H; 7.71 (dl, J=8.5) 2H; 7.64 (dl, J=8.5) 2H; 7.60 (dl, J=9) 1H; 7.37 (dl, J=9.5) 1H; 7.02 (dl, J=8.5) 2H; 6.97 (dl, J=8.5) 2H; 6.65 (dl, J=8.5) 2H; 4.90 (m) 1H; 4.77 (m) 1H; 4.66 (m) 1H; 4.45 (m) 1H; 4.42 (m) 1H; 4.39 (m) 1H; 4.34(sl) 1H; 4.26 (m) 1H; 4.22 (m) 1H; 4.08 (m) 1H; 4.01 (t, J=6.5) 2H; 3.88 (m) 3H; 3.70 (m) 2H; 3.51 (m) 2H; 3.48 (m) 1H; 3.31 (m) 2H; 3.28 (m) 1H; 3.16 (m) 2H; 2.53 (dd, J=6 et 13.5) 1H; 2.44 (dd, J=7.5 et 13.5) 1H; 2.27 (m) 1H; 2.25 (m) 1H; 2.15 (m) 2H; 1.94 (m) 1H; 1.74 (m) 2H; 1.44 (m) 2H; 1.22 to 1.40 (m) 8H; 1.13 (d; J=6) 3H; 0.99 (d, J=6.5) 3H; 0.88 (t, J=7) 3H.

EXAMPLE 15

1-[4-[(aminoiminomethyl)hydranol]-n2-[[4-[4-[4-(pentyloxy)-phenyl]-1-piperazinyl]phenyl]carbonyl]-L-ornithine]-4-[4-(4hydroxyphenyl)-L-threonine]-5-L-serine-echinocandin B Stage A: 1-[(4R,5R)-4.5-dihydroxy-N2-[[4-[4-[4-(pentyloxy)phenyl]-1-piperazinyl]phenyl]carbonyl]-L-ornithine]-4-]4-(4-hydroxy-phenyl)-L-serine echinocandin B 1-Preparation of the Ester 55 mg of pentafluorophenol and 61 mg of N,N' dicyclohexyl carbodiimide is added to a mixture of 100 mg of [4-[4-[4-(pentyloxy)phenyl]-1-piperazinyl]phenyl]carboxylic acid and 3 ml of tetrahydrofurane. The reaction compound is stirred at 20° C. for 16 hours, filtered, washed with THF and concentrated dry. It is placed in diethylic ether, filtered, washed and concentrated. 71 mg of product is obtained.

2-Coupling

A suspension containing 71 mg of the ester above, 70 mg of deoxymulundocandin <<nucleus>> obtained as in preparation 2, 2.5 ml of DMF in the presence of 4A activated siliporite is stirred at 20° C. for one night. It is concentrated, the product obtained is placed in ether and filtered. A product is obtained that is chromatographed on silica by eluting with the mixture acetonitrile/water/trifluoroacetic acid (60-40-0.02). 30 mg of sought product is thus obtained.

Stage B: 1-[N2-[[4-[4-[4-(pentyloxy)phenyl]-1-piperazinyl]-phenyl]-carbonyl]4-oxo-L-ornithine]-4-[4-(4-hydroxyphenyl)-L-threonine]-5-L-serine echinocandin B 1-Preparation of the Ester A mixture of 1 g of the product of stage A, 25 ml of acetonitrile, in the presence of 4A activated siliporite is heated to 55° C. 430 ml of trimethylsilane iodide is added. It is stirred for 45 minutes then 150 µl of an aqueous solution of sodium thiosulphate at 30% is added. It is stirred for 40 minutes at 20° C. and concentrated. The dry extract is placed in water, stirred for 1 hour at 20° C. spun and washed. A product is obtained that is chromatographed on silica by eluting with the compound methylene chloride-methanol-water (86/13/1). 497 mg of sought product are obtained. Yield 42%.

Stage C: 1-[4-[(aminoiminomethyl)hydrazono]-N2-[[4-[4-[4-(pentyloxy)-phenyl]-1-piperazinyl]phenyl]carbonyl]-L-ornithine]-4-[4-(4-hydroxyphenyl)-L-threonine]-5-L-serine-echinocandin B A suspension containing 400 mg of the product of stage B, 4.8 ml of n-butanol and 221 mg of aminoguanidine hydrochloride is heated at 130° C. for 3 hours. It is concentrated and 705 mg of a product is obtained that is chromatographed on silica by eluting with the methylene chloride methanol compound 85/15, then by semi-preparative HPLC (kromasil C18) with a 40.60.0.02) acetonitrile/water/trifluoroacetic acid compound. 64 mg of sought product is thus obtained.

NMR Spectrum (CDCl$_3$)

10.75(s) 0.66H; 10.45(s) 0.33H; 8.39 (d, J=8) 0.33H; 8.34(m) 1H; 8.10 (d, J=7.5) 0.66H; 8.08 (d, J=8) 0.33H; 7.99 (d, J=8.5) 0.66H; 7.74 (d, J=8.5) 1.33H; 7.71 (d, J=8.5) 0.66H; 7.60 (d, J=8.5) 0.66H; 7.50 (m) 1.33H; 7.00 (m) 6H; 6.86 (d, J=8.5) 2H; 6.65 (d, J=8) 2H; 5.08 (dt, J=2 et 11.5) 0.66H; 4.94 (m) 1H; 4.88(m) 0.33H; 4.75 (dm, J=8) 0.33H; 4.67 (dd, J=3 et 7.5) 0.66H; 4.43 (m) 1H; 4.38 (m) 1.66H; 4.33 (m) 0.66H; 4.26 to 4.20 (heavy) 2.33H; 4.12 (d, J=9) 0.66H; 4.00 to 3.68 (heavy) 7.33H; 3.90 (t, J=7) 2H; 3.62 (d, J=12) 0.33H; 3.43 (swide) 2H; 3.30 to 3.20 (m) 1H; 3.20 (swide) 2H; 2.91 (d, J=14) 0.66H; 2.86 (m) 0.33H; 2.76 (m ) 0.33H; 2.63 (dd, J=14 et 12.5) 0.66H; 2.52 (dt, J=6 et 13) 1H; 2.44 (dd, J=8 and 13) 1H; 2.35 (m ) 0.33H; 2.25 (m ) 1.66H; 1.93 (twide,J=13) 1H; 1.69 (m) 2H 1.42 to 1.30 (heavy) 4H; 1.15 (d, J=6) 1.98H; 1.10 (,J=6) 0.99H; 0.98 (d, J=6.5) 3H; 0.90 (t, J=7) 3H.

EXAMPLE 16

1-[4-[(2-aminoethyl)amino]-N2-[4-[4"-(pentyloxy) [1.1':4'1"-terphenyl]-4yl]carbonyl]-L-ornithine]-4-[4-(hydroxphenyl)-L-threonine]5-L-serine-echinocandin B (isomer A and isomer B)

Operating as previously, from deoxy-mulundocandin <<nucleus>> prepared as indicated in preparation 2 by obtaining 1-[(4R, 5R)-4.5-dihydroxy-N2-[[4"-(pentyloxy) [1.1': 4',1"-terphenyl]-4-yl]carbonyl]-L-ornithine]-4-[4-(4-hydroxyphenyl-L-threonine]-5-L-serine B and the corresponding 4-oxo derivative as intermediate product, the sought product is obtained.

NMR Spectrum (CDCl$_3$)

9.00 (wide) 1H; 8.37 (dl, J=8.5) 1H; 8.28 (m) 1H; 8.10 (dl, J=6) 1H; 8.02 (dl, J=8) 2H; 7.82 (m) 4H; 7.73 (dl, J=8) 2H; 7.66 (dl, J=8) 2H; 7.38 (dl, J=9) 1H; 7.32 (dl, J=9) 1H 7.03 (dl, J=8.5) 2H; 6.96 (dl, J=8) 2H; 6.66 (dl, J=8) 2H; 5.03 (m) 1H; 4.84 (m) 1H; 4.67 (m) 1H; 4.45 (m) 2H; 4.36 (dd, J=7.5 and 10.5) 1H; 4.23 (m) 2H; 4.18 (sl) 1H; 4.04 (m) 1H; 4.02 (t, J=6.5) 2H; 4.00 (m) 1H; 3.87 (dl, J=9.5) 1H; 3.76 (m) 1H; 3.72 (m) 2H; 3.55 (m) 1H; 3.44 (m) 1H; 3.35 (m) 2H; 3.30 (m) 1H; 3.19 (m) 2H; 3.12 (m) 1H; 2.53 (m) 1H; 2.45 (m) 1H; 2.12 to 2.30 (m) 3H; 1.90 to 2.05 (m) 2H; 1.74 (m) 2H; 1.30 to 1.55 (m) 4H; 1.20 (d, J=5.5) 3H; 0.96 (d, J=6.5) 3H; 0.91 (t, J=7) 3H.

EXAMPLE

Pharmaceutical Composition

| Tablets have been prepared containing: | |
|---|---|
| The product of example 14 | 150 mg |
| Excipient q.s.p. | 1 g |

(Details of the excipient: starch, talc, magnesium stearate).

Pharmacological Study

A—Inhibition of the Glucane Synthesis of *Candida Albicans*.

The membranes of *Candida albicans* are purified according to the process described by Tang and al Antimicrob. Agents Chemother 35, 99–103, 1991. 22.5 µg of membrane proteins are incubated in a mixture of 2 Mm of 14C-UDP glucose (specific activity=0.34 mCi./mmol, 50 µg of α-amylase, 1 Mm of dithiotreitol (DTT), 1 Mm EDTA, 100 Mm NaF, 7 µM of GTP-γ-S, 1M of sucrose and 5 oMm OF Ttris-HCL (pH 7.8) in a volume of 100 µl. The medium is incubated at 25° C. for 1 hour and the reaction terminated by addition of TCA to a final concentration of 5%. The reaction medium is transferred onto a pre-humidified glass fibre filter. The filter is washed, dried and its radioactivity is counted.

Mulundocandin is used as positive control.

The control of the medium is carried out with the same quantity of DMSO 1%. The obtained results show that the products of the invention present a good activity in this test, particularly the products of examples 9, 11, and 14.

B—activity on the Enzyme *Aspergillus fumigatus*.

The enzyme is prepared according to the Beaulieu et al. (Antimicrob. Agents Chenother 38, 937–944, 1994) process. The protocol used is identical to the protocol described above for the enzyme *Candida albicans* except that dithiotreitol is not used in the reaction medium.

The products present a good activity in this test.

The invention claimed is:

1. A compound of the formula:

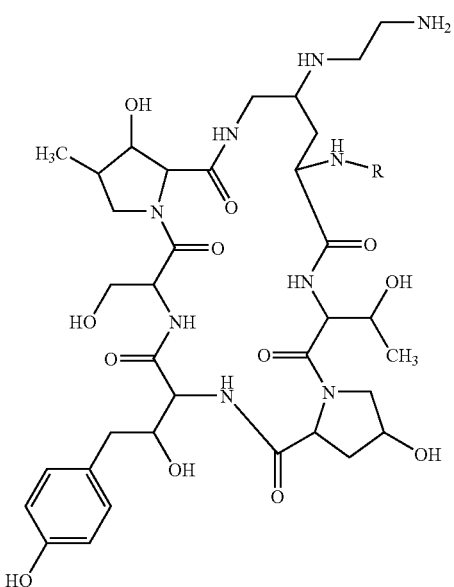

wherein R is

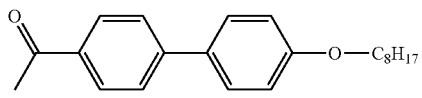

or a pharmaceutically acceptable acid addition salt thereof.

2. A pharmaceutical composition comprising a compound of claim 1 or a pharmaceutically acceptable acid addition salt thereof and a pharmaceutically acceptable carrier.

3. The method of claim 2 in which said pharmaceutically acceptable carrier comprises apyrogenic sterile water.

4. The pharmaceutical composition of claim 2 which is in the form of a sugar coated tablet, capsule, granule, suppository, injectable preparation, ointment, cream or gel.

5. A method of treating an ailment caused by exposure to a fungus comprising administering to a person in need thereof a pharmaceutical composition according to claim 2.

6. A method of treating an ailment in a person caused by exposure to a fungus comprising administering to a person in need thereof an antifungally effective amount of a compound of claim 1.

7. The method of claim 6 in which said fungus is selected from the group consisting of *Candida albicans, Candida glabrate, Candida krusei, Candida tropicalis, Candida pseudotropicalis, porapsilosis, Aspergillus fumigatus, Aspergillus flavus*, and *Cryptococcus neoformans*.

8. The method of claim 6 in which said ailment is selected from the group consisting of digestive, urinary, vaginal or cutaneous candidoses, cryptococcoses, neuromenengeal, pulmonary or cutaneous cryptococcoses, bronchopulmonary and pulmonary aspergilloses and invasive aspergilloses in an immunocompromised subject.

9. The method of claim 6 which is directed to the treatment of mycosic ailments in people with congenital or acquired immune compromise.

10. The method of claim 6 in which the effective amount ranges from about 50 mg to about 300 mg per day.

11. A method of treating an ailment caused by exposure to a fungus comprising administering to a person in need thereof an antifungally effective amount of a compound of claim 1.

* * * * *